United States Patent [19]

Cole

[11] Patent Number: 5,665,924

[45] Date of Patent: Sep. 9, 1997

[54] GAS SAMPLING POINT FOR SMOKE/ POLLUTION DETECTION SYSTEM

[75] Inventor: Martin Terence Cole, Keysborough, Australia

[73] Assignee: I.E.I. PTY. Ltd., Clayton, Australia

[21] Appl. No.: 662,490

[22] Filed: Jun. 13, 1996

Related U.S. Application Data

[63] Continuation of Ser. No. 335,787, Nov. 10, 1994, abandoned.

[30] Foreign Application Priority Data

May 14, 1992 [AU] Australia ............................ PL 2452
Feb. 22, 1993 [AU] Australia ............................ PL 7435

[51] Int. Cl.$^6$ ............................................... G01N 1/22
[52] U.S. Cl. .......................... 73/864.73; 73/863.85; 73/863.81
[58] Field of Search ................... 73/863.81, 863.86, 73/863.85, 864.74, 864.73; 411/340, 341, 342, 182

[56] References Cited

U.S. PATENT DOCUMENTS

| | | | |
|---|---|---|---|
| 3,799,670 | 3/1974 | Kohr | 356/439 |
| 4,197,781 | 4/1980 | Giannuzzi | 411/341 |
| 4,218,918 | 8/1980 | Ueno et al. | 73/863.85 |
| 4,456,014 | 6/1984 | Buck et al. | 73/863.86 |
| 4,657,212 | 4/1987 | Gilmore et al. | 411/342 |
| 4,821,585 | 4/1989 | Kempe | 73/863.85 |
| 4,878,790 | 11/1989 | McSherry et al. | 411/340 |
| 4,974,455 | 12/1990 | McGowan et al. | 73/863.81 |
| 4,978,265 | 12/1990 | De Wan | 411/182 |
| 5,249,900 | 10/1993 | Mitts | 411/182 |
| 5,297,432 | 3/1994 | Traina et al. | 73/863.83 |

*Primary Examiner*—Hezron E. Williams
*Assistant Examiner*—Nashmiya Ashraf
*Attorney, Agent, or Firm*—Learman & McCulloch

[57] ABSTRACT

A sampling point (110) for use in a pollution/smoke detection system for fixture to an apertured panel in a building, this system including a plurality of said sampling points (110) for connection to an aspirated gas reticulation system for drawing gas from said sampling points (110) exposed to a space under surveillance, said sampling point including a portion (19) for securement to a retaining means (10) and a capillary tube (15a) communicating between the sampling point (110) and said aspirated gas reticulation system, the sampling point (110) having an orifice (116) of a predetermined size to communicate between an area to be surveyed and the gas reticulation system, said capillary tube (116) conforming to standard smoke detection requirements as to bore strength flexibility and crush resistance, said sampling point (110) being adapted to be fitted from either the visible or blind side of the apertured panel and including collapsible shroud means (17, 18) capable of passing through said apertured panel and expanding to hide the panel aperture from which it has emerged. A cover (117) releasably fitted to an apertured mounting base (111) and a capillary tube (113) for communicating the mounting base (111) and the gas reticulation system through an aperture, wherein the mounting base (111) and the cover (117) interconnect with a press fit, said cover (117) comprising an aesthetically formed shroud for the sampling point (110), is also disclosed.

6 Claims, 7 Drawing Sheets

GAS SAMPLING POINT FOR SMOKE/POLLUTION DETECTION SYSTEM

This application is a continuation of copending applications Ser. No. 08/335,787 filed on Nov. 10, 1994, now abandoned; International Application PCT/AU93/00207 filed on May 10, 1993 and which designated the U.S.

The present invention relates to a sampling point for use in pollution and smoke detection systems and specifically very early warning smoke detection apparatus.

BACKGROUND OF THE INVENTION

Sampling points are used to penetrate a wall or ceiling and in operation are coupled to a capillary tube which is in turn connected to a pipe system distributed throughout a building or the like for drawing gas samples from the various sampling points to a pollution detection system.

It is important that the sampling points for smoke detectors are strategically positioned to ensure collection of smoke at the earliest possible moment. It is therefore possible or usual for the sample point to be located in conspicuous positions in the room of a building, necessitating good aesthetic appearance of the sampling point.

Furthermore it is important that the fitting of such sampling points is a relatively simple operation and yet the device must comply with various standards, for example Australian Standard 1670 which amongst other things calls for penetration of the sampling point for at least 25 mm into the space to be surveyed and the provision of a 50 mm identification ring in the case of use in smoke detection apparatus. It is an objective of the present invention to provide an improved sampling point construction complying with standard requirements has a minimum number of parts, and is simple to manufacture and install.

SUMMARY OF THE INVENTION

There is provided according to the present invention a sample point for use in a pollution/smoke detection system for fixture to an apertured panel in a building, this system including a plurality of said sampling points for connection to an aspirated gas reticulation system for drawing gas from said sampling points exposed to a space under surveillance, said sample point including a portion for securement to a retaining means and a capillary tube communicating between the sampling point and said aspirated gas reticulation system, the sampling point having an orifice of predetermined size to communicate between an area to be surveyed and the gas reticulation system, said capillary tube conforming to standard smoke detection requirements as to the bore strength flexibility and crush resistance, said sampling point being adapted to be fitted from either the visible or blind side of the apertured panel and including collapsible shroud means capable of passing through said apertured panel and expanding to hide the panel aperture from which it has emerged.

In a further aspect of the invention there is provided a sample point adapted to be fixed to an apertured panel or the like in a building for use in a pollution/smoke detection system in the building, the system including a plurality of sample points for connection to an aspirated gas reticulation system for drawing gas from said sampling point exposed to a space under surveillance, said sampling point including a retention member for securing a capillary tube to communicate between the sampling point and said reticulation system, the arrangement being such that the capillary tube can be fitted from either the visible or blind side of the apertured panel or the like wherein the sample point includes a collapsible shroud means adapted to pass through said apertured panel or the like for fitment of the sampling point from the blind side of the aperture, said shroud means being expandable upon passing through the aperture to form a cover for the aperture.

There is provided according to a further aspect of the present invention a sample point for use in pollution/smoke detection system comprised of a two part construction including an apertured mounting base for fixture to a base surface such as a ceiling for connection to an aspirated gas reticulation system for drawing gas from a plurality of sampling points and a cover loosely fitted to said mounting base and a capillary tube including an aperture for communicating with said apertured mounting base and gas reticulation system, wherein the mounting base and cover interconnect with a press fit, said cover comprising an aesthetically formed shroud for the sample point.

Conveniently the shroud is collapsible in one direction only to enable it to support or absorb axial loads applied thereto in the opposing direction.

Conveniently the collapsible shroud means includes a part releasably secured to said retaining portion on said sampling point, and hinged radially extending members thereon are adapted to retract when passing through the panel aperture and to expand radially to form said shroud in the manner of an unfolding umbrella.

The retaining portion is preferably threaded and is split longitudinally to provide clamping means for rapid and secure fixing of the capillary tube. Said clamping means is engaged by encircling the threaded portion of the sampling point with the shroud member which forces clamping teeth to squeeze into the capillary tube. Below said clamping means the threaded tube is tapered internally to form a tight seal between said nozzle and said capillary tube when assembled avoiding the need for additional parts such as an O-ring to provide the seal.

The retaining member and the shroud members preferably include partial thread portions which allow ratcheting of the components over the threaded portion but still provide adequate tightening of the components when screwed together to achieve a secure fitting. The partial thread portion facilitates the ratcheting and quick assembly of components onto the threaded portion of the sampling point avoiding the need to turn the sample point and thereby twist the capillary tube.

THE DRAWINGS

The invention will be described in greater detail with reference to the accompanying drawings in which.

3

DETAILED DESCRIPTION

Figure 1:
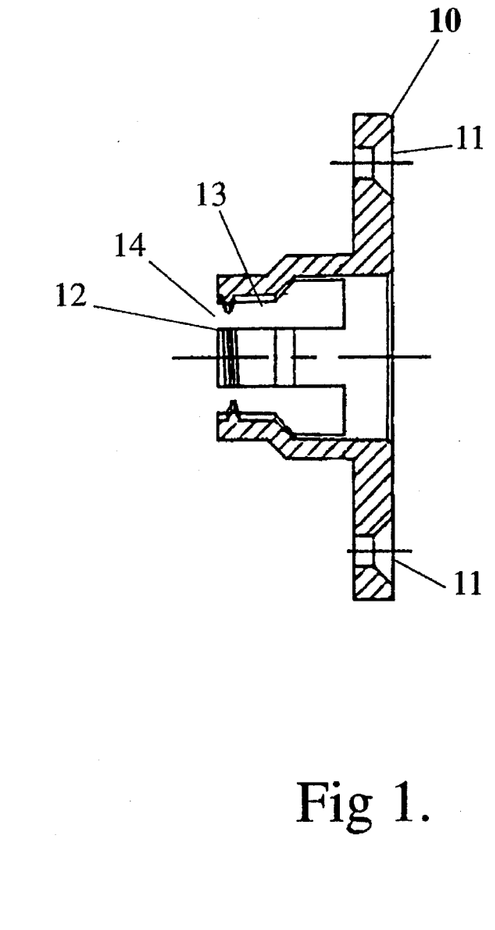
FIG. 1 is a sectional view of a retaining member taken on the line A—A of FIG. 2.
Figure 2:
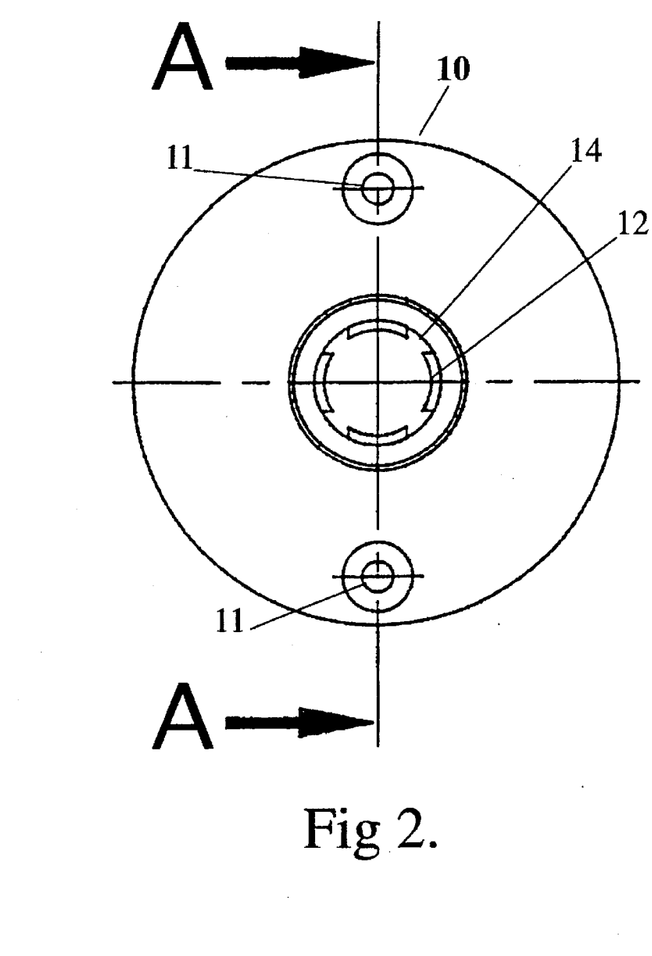
FIG. 2 is a plan view of the member shown in FIG. 1.

With reference to FIGS. 1 and 2, these figures depict a retaining member 10 formed of flexible resilient material and which can be affixed to a wall or panel through holes 11 fixed to either the visible or blind side of the wall or panel.

The retaining member includes a partial thread portion 12 in bore 13 for threaded attachment to a threaded nozzle member which will be described in further detail later.

The bore of the retaining member 10 is split at reference 14 to enable flexible movement of the tube member and enable it to ratchet over the thread of the threaded nozzle member 16 which will be described in greater detail later.

Figure 3:
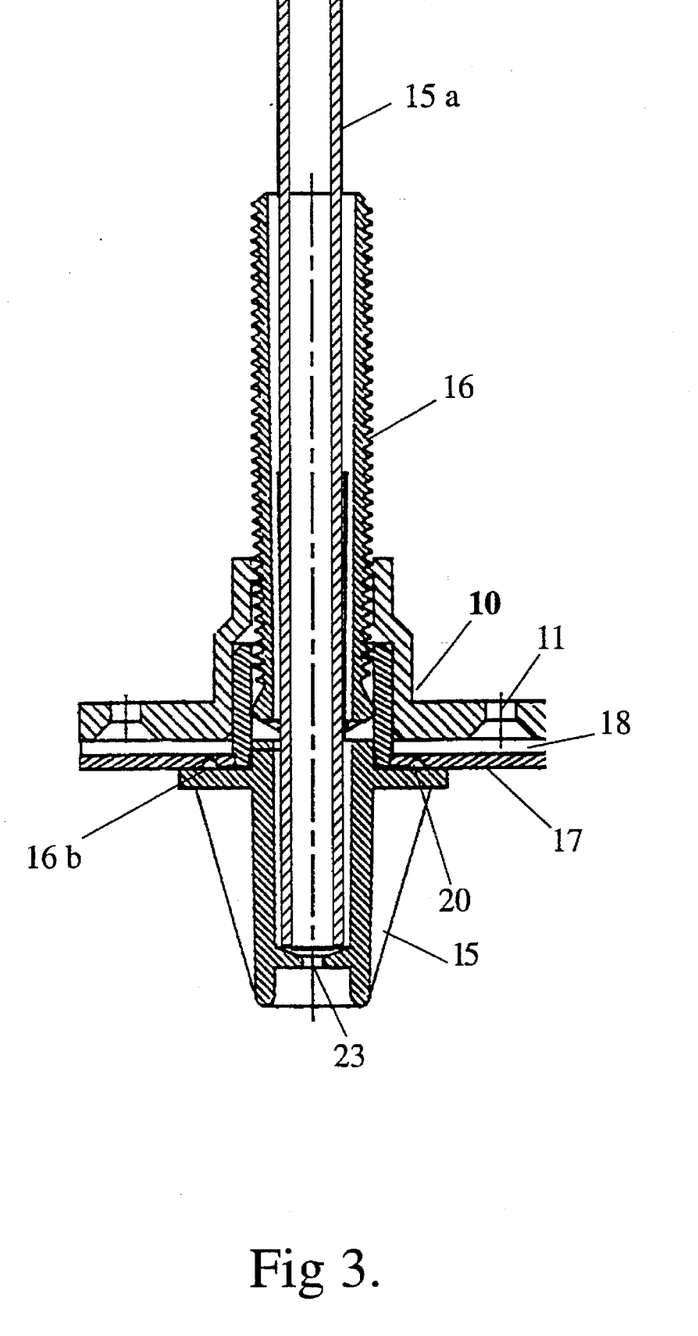
FIG. 3 is an assembly view of a sample point including a capillary tube, clamping means, retaining member and a pair of daisy shroud members all in cross-section.

FIG. 3 shows an assembly drawing with the retainer member which may be secured to a visible side of a panel or the like not shown coupled with a capillary tube 15a fitted into the threaded nozzle member 16. The arrangement shown in FIG. 3 can be fitted from within a room by affixing the retaining member 10 to a wall or ceiling panel to which can then be fitted the threaded nozzle member 16. The threaded nozzle member 16 is slightly tapered internally to form a tight seal between said nozzle and the capillary tube at the leading edge of the capillary tube.

According to the invention a daisy shroud member is made up of the components shown in FIGS. 5–8 in which upper and lower daisy members 17 and 18 are provided with circumferentially spaced petals 19 which in unstressed condition form a flange that is substantially normal to the axis of the nozzle and in which the petals of one daisy member occupies the spaces between the petals of the other. The petals 19 are hinged by a plastic hinge at 20 to be folded along an axial direction to allow the daisy shroud to be inserted into a wall aperture such as that shown in FIG. 4 in a folded umbrella like position and when it emerges from the hole the petals 19 spring out in the manner of an opening umbrella into a radial flare or fan pattern to form a shroud over the hole.

Figure 4:
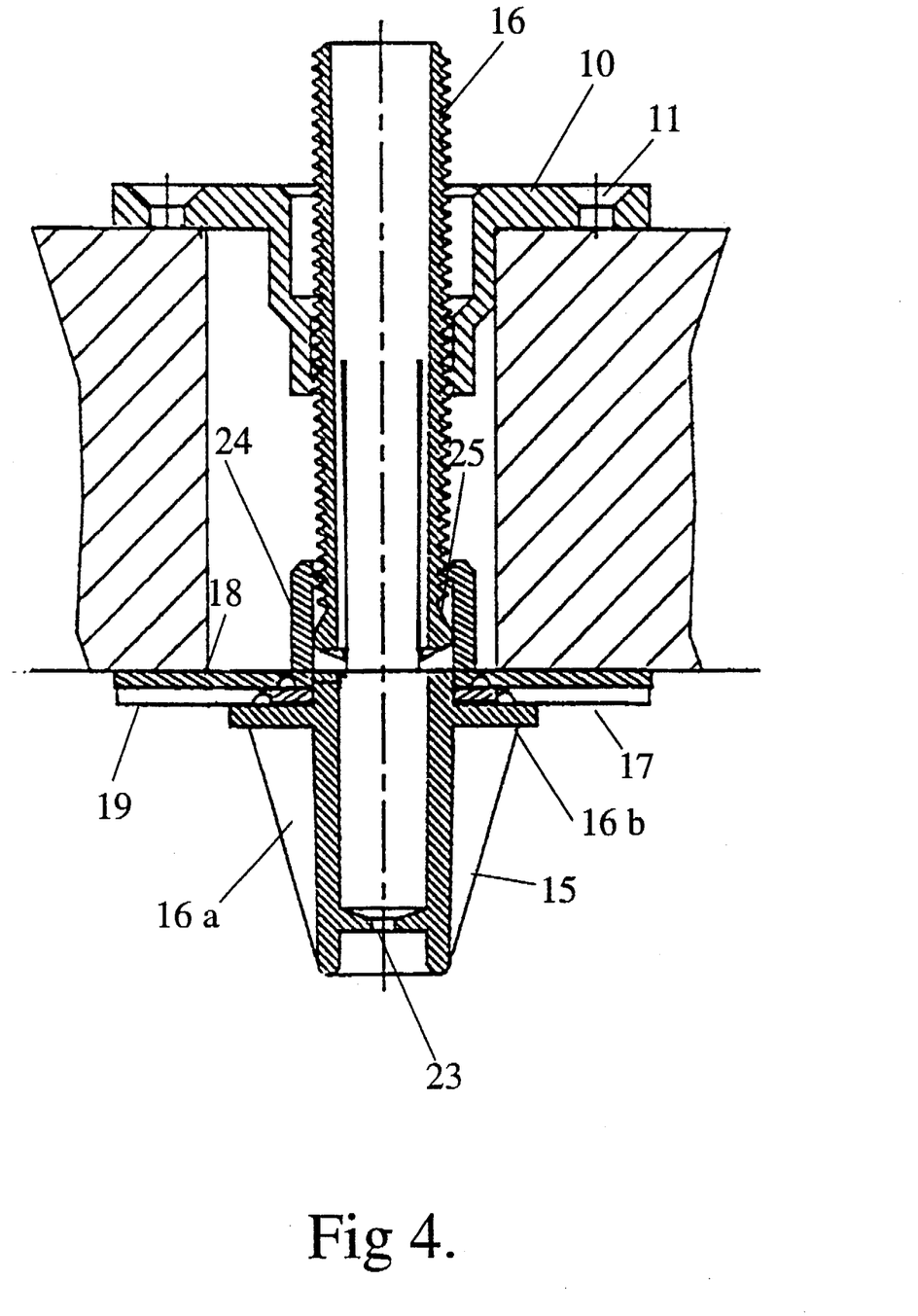
FIG. 4 is a sectional view similar to FIG. 3 but showing the majority of the parts shown in FIG. 3 accommodated in an aperture in a thick panel.

FIG. 4 shows an alternative mounting version wherein the retaining member 10 is inverted, spaced from the daisy shrouds 17 and 18, and secured to the blind side of an apertured wall from which the capillary tube and nozzle member 16 may be suspended.

Figure 5:
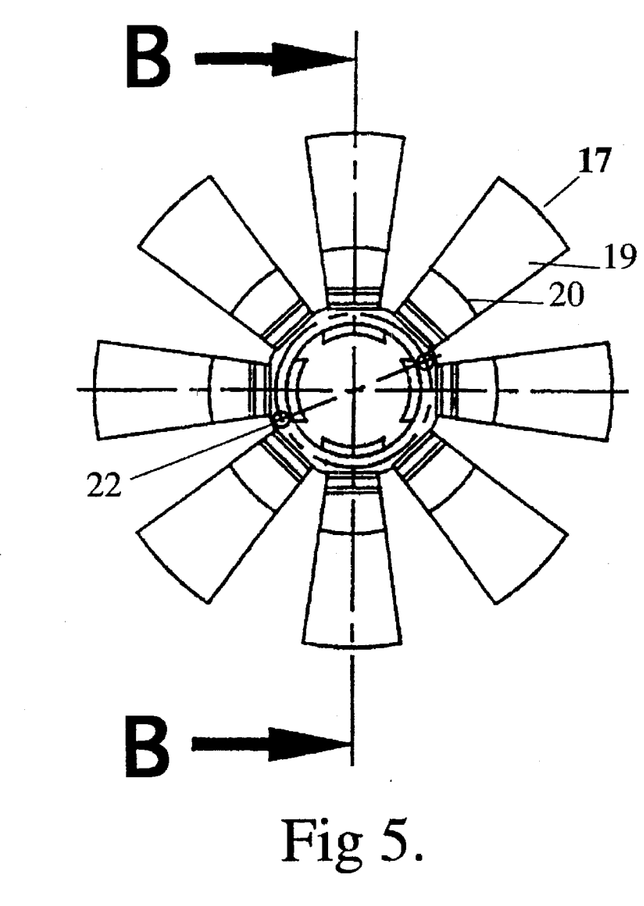
FIG. 5 is a plan view of the upper daisy shroud.
Figure 6:
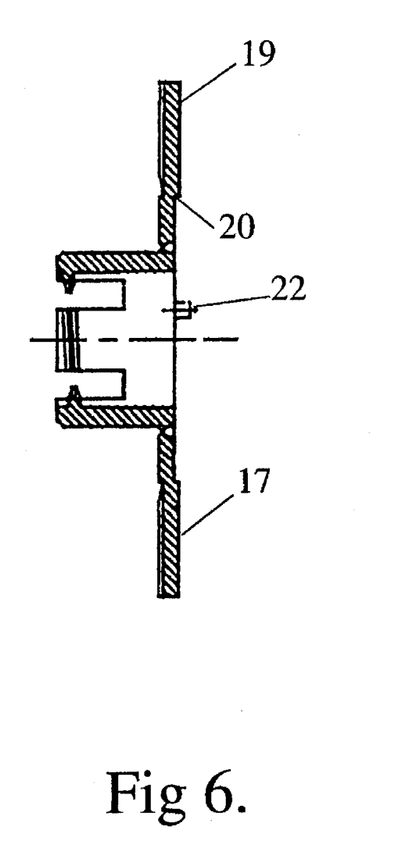
FIG. 6 is a sectional view taken on the line B—B of FIG. 5.

According to the invention a daisy shroud member made up of the components shown in FIGS. 5 to 8 are provided in which the daisy shroud members 17 and 18 have petals 19 which are hinged by a plastic hinge at 20 to be folded along an axial direction to allow the daisy shroud to be inserted into a wall aperture such as that shown in FIG. 4 in a folded position and when it emerges from the hole the petals 19 spring out into a radial flare to form a shroud of the hole. With reference to FIGS. 4 and 6 the tubular portion 24 is of such diameter to engage clamps 25 on the nozzle member 16 and thus provide a clamping effect onto the capillary tube when installed. With reference to FIG. 4 the positioning of the nozzle member 16 in the wall aperture allows flexibility of centering of the sampling point with respect to the panel and any accidental misalignment in the wall aperture.

Figure 7:
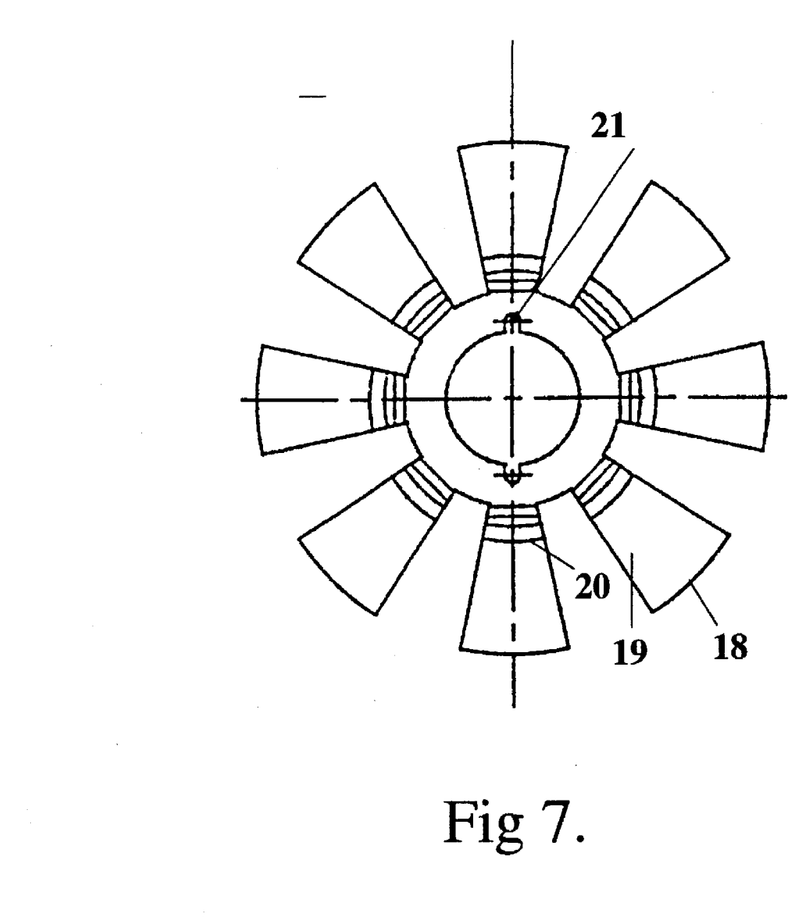
FIG. 7 is a plan view of the lower daisy shroud member.
Figure 8:
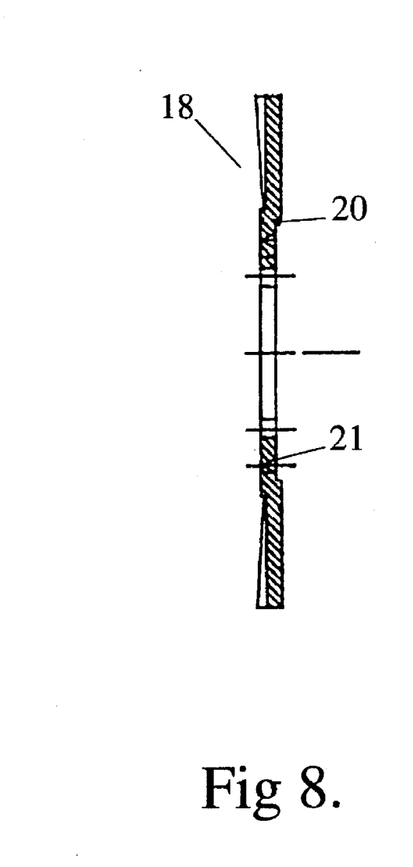
FIG. 8 is a sectional view taken on the line C—C of FIG. 7.
Figure 9:
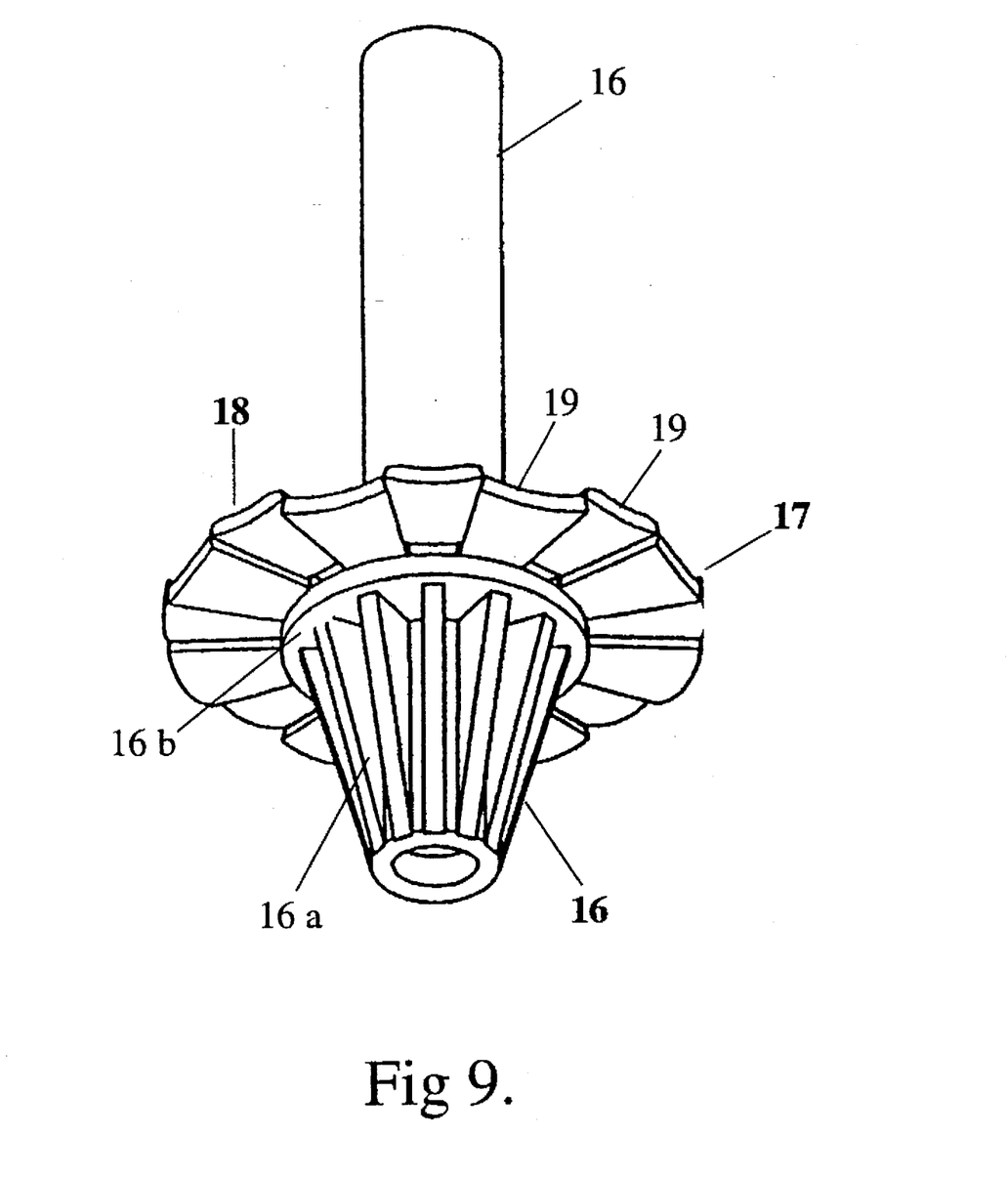
FIG. 9 is a partial perspective view of the assembly of FIG. 3 without threads and omitting the retaining member and the capillary tube.
Figure 10:
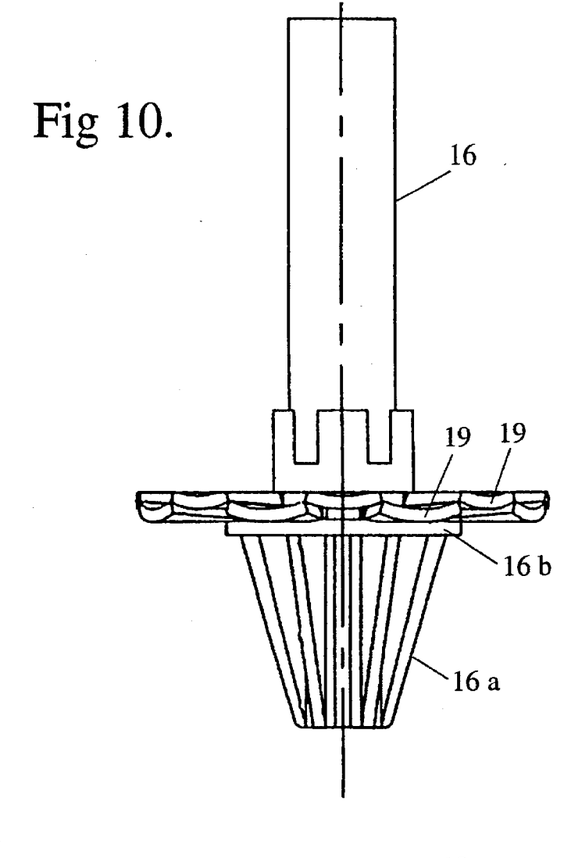
FIGS. 10 and 11 are elevational and plan views of the assembly of FIG. 9.
Figure 11:
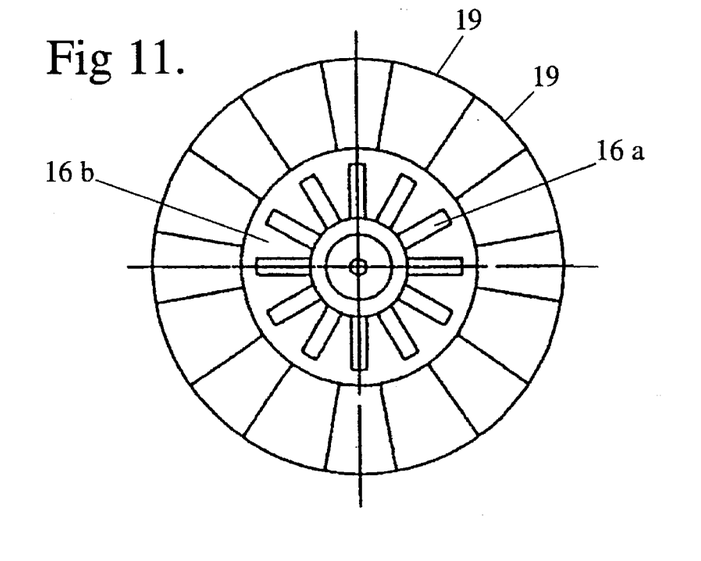

The two components 17, 18 of the shroud incorporate a pin and matching aperture at 21, 22 to lock the two components together when fitted together so that the petals overlap one another to form a complete shroud having the diameter shown in FIGS. 5 and 7.

The shroud members 17, 18 are fitted between the capillary tube and the wall or ceiling panel as shown in FIG. 4 or alternatively where the retaining member is also secured on the same side of the ceiling or wall, the daisy shroud members are sandwiched between the sampling member 15 and the retaining member 10. In each instance the shroud provides a decorative cover for the aperture as shown in FIG. 4 or the retaining member 10 as shown in FIG. 3.

The hinge of the daisy members is arranged so that the folding of the petals 19 may only be in a single direction to provide mechanical support for the various components when tightened up onto the retaining member.

The sampling tube 15 may be formed with ribs 16a or the like to provide a decorative finish to improve the aesthetic appearance of the sampling point.

With reference to FIGS. 1 and 2 of the drawings, the retaining member 10 has a split tubular section 14 having a partial thread 12 on the internal bore of the tubular section which is intended to engage with the nozzle member 16 as shown in FIGS. 3 and 4. The arrangement is such that the retaining member can be forced over the threaded portion for fast securement and then turned to tighten up on the thread.

A similar arrangement is provided with the tubular portion of the daisy shroud member as shown in FIG. 6. The retaining member 10 includes apertures for receiving fixing screws not shown for fixing the retaining member to a panel or like structure as shown in FIGS. 3 and 4. The sampling point includes an orifice 23 for allowing passage of a sample air or gas into the capillary tube mounted within the sample point.

With reference to FIGS. 3 and 4 the sampling point includes a radially extending flange 16b which extends beyond the hinge points 20 on the daisy shroud members to facilitate tightening of the sample point to the panel and prevent any over bending of the panels which could possibly affect the final appearance of the installed sample point.

It will be appreciated that the sampling point of the invention can be easily fitted from inside or outside a panel depending upon access without any difficulty and wherein the components are quickly and easily secured together in an air tight and secure manner.

The claims defining the invention are as follows:

1. A gas sampling point construction adapted to be mounted on a panel having an aperture therethrough, said construction comprising a tubular member of such size as freely to be accommodated in said aperture; a capillary tube accommodated in said tubular member, said capillary tube and said tubular member having open opposite ends to enable a sample of gas to pass therethrough; shroud means carried by said tubular member, said shroud means including a flange having an unstressed condition in which said flange may overlie and extend beyond said aperture and being formed of resilient material enabling said flange to assume a collapsed condition for passage through said aperture, the resilience of said material enabling said flange to return to said unstressed condition following passage through said aperture; and retention means for securing said tubular member and said shroud means to the panel, the construction and arrangement of said shroud being such that the sampling point construction may be inserted into the aperture from either end thereof and slid through the aperture to a position in which said flange in said unstressed condition provides an aesthetic cover for one end of said aperture.

2. The construction according to claim 1 wherein said flange is hinged to move in one direction only from said unstressed condition.

3. The construction according to claim 1 wherein said shroud is composed of two overlying flanges each of which has a plurality of circumferentially extending petals separated from one another by spaces, the petals of one of said two flanges occupying the spaces between the petals of the other of said two flanges.

4. The construction according to claim 1 wherein said retention means includes a threaded sleeve in threaded engagement with said tubular member.

5. The construction according to claim 4 wherein said threaded sleeve is split along the length thereof.

6. The construction according to claim 4 wherein said threaded sleeve is formed of material sufficiently flexible and resilient to enable said sleeve to be axially slideable relative to said tubular member.

* * * * *